(12) United States Patent
Sica et al.

(10) Patent No.: US 7,339,040 B2
(45) Date of Patent: Mar. 4, 2008

(54) DNA MOLECULES OPTIMIZED SEQUENCES THAT ENCODE THE IA-2IC ANTIGEN, RNA MOLECULES, EXPRESSION VECTORS, TRANSFORMED CELLS, METHOD OF PREPARING THE IA-2IC ANTIGEN, POLYPEPTIDE OF THE HUMAN IA-2IC ANTIGEN, AND IN VITRO PROCEDURE AND KIT FOR THE DIAGNOSIS OF AUTOIMMUNE DIABETES

(75) Inventors: Mauricio Pablo Sica, Buenos Aires (AR); Maria Evangelina Primo, Santa Fe (AR); Mario Roberto Ermácora, Buenos Aires (AR); Edgardo Poskus, Buenos Aires (AR)

(73) Assignees: Laboratorio ELEA S.A.C.I.F.y.A., Buenos Aires (AR); Consejo Nacional de Investigaciones Cientificas y Tecnicas (CONICET), Buenos Aires (AR)

( * ) Notice: Subject to any disclaimer, the term of this patent is extended or adjusted under 35 U.S.C. 154(b) by 753 days.

(21) Appl. No.: 10/345,307

(22) Filed: Jan. 16, 2003

(65) Prior Publication Data

US 2005/0089848 A1    Apr. 28, 2005

(51) Int. Cl.
*C07H 21/02*  (2006.01)
*C07H 21/04*  (2006.01)

(52) U.S. Cl. .................. 536/23.1; 435/69.1; 435/252.3; 435/320.1

(58) Field of Classification Search ...................... None
See application file for complete search history.

(56) References Cited

OTHER PUBLICATIONS

Sica, M.P., et al. Biotechnol. Appl. Biochem. 2003;37:301-309.*
Attwood, T.K., Science. 2000;290:471-473.*
Skolnick, J. and Fetrow, J.S. TBTech. 2000;18:34-39.*

* cited by examiner

*Primary Examiner*—G. R. Ewoldt
(74) *Attorney, Agent, or Firm*—Birch, Stewart, Kolasch & Birch, LLP

(57) ABSTRACT

Otimized DNA molecules that encode human IA-2ic, wherein at least one of the codons starting at positions 2747 and 2816 of the complete IA-2 gene is CGT. Said molecules are useful for detecting insulin-dependent (type 1) diabetes mellitus, and may be fused to auxiliary proteins or peptides (for example, His-tag). RNA molecules encoded by the optimized DNA molecules, expression vectors comprising the optimized DNA molecules and cells transformed with said DNA molecules (particularly *Escherichia coli* cells). Also a method of producing human IA-2ic antigen that comprises growing cells transformed with the said optimized nucleic acid molecules under conditions suitable for producing said protein, the polypeptide obtained through that procedure, and an in vitro diagnostic method and a diagnostic kit using it.

14 Claims, 9 Drawing Sheets

Figure 8

| Name | Sequence |
|---|---|
| 2797c | ctgcagtgatggtgccggcCgTaccg |
| 2797cDG | ctgcagtgGtggtgccggcCgTaccg |
| 2741cF | ttccgcCgTaaggtgaacaagtgctac |
| 2741cR | tgttcaccttAcGgcggaagtccagcag |
| A877D | ctcacgcagttccacttcctcagctggccggATgagggtacaccg |
| IcNde | CATATGcggcaacaagacaaggagcg |
| IcaR | cagtgaggagtgggtacacagagatg |
| IcaF | gcggcagcaagacaagagcg |
| 3'THisBam | GGATCCTCAGTGATGGTGATGGTGATGGCTGCCGCGCGGCACCAGctggggaagggccttgag |
| 3095BamHI | cagtgaggagtgggATcCcagagatg |
| KozIC | TCTAGACCACCATGGCgcgAcagcaagacaaagagcg |

DNA MOLECULES OPTIMIZED SEQUENCES THAT ENCODE THE IA-2IC ANTIGEN, RNA MOLECULES, EXPRESSION VECTORS, TRANSFORMED CELLS, METHOD OF PREPARING THE IA-2IC ANTIGEN, POLYPEPTIDE OF THE HUMAN IA-2IC ANTIGEN, AND IN VITRO PROCEDURE AND KIT FOR THE DIAGNOSIS OF AUTOIMMUNE DIABETES

The present invention relates to the production of antigens useful for the immunodiagnosis of diabetes mellitus. More particularly, the invention relates to optimized DNA sequences that encode the IA-2ic antigen.

Insulin-dependent (type 1) diabetes mellitus is characterized by the autoimmune destruction of insulin-producing β cells. During the prodrome of type 1 diabetes, a variety of autoantibodies, called markers, is generated, some of which persist long after the complete development of the disease, and which are a valuable aid for its early detection [1-4]. The best characterized markers are those directed against glutamic acid decarboxylase (GAD) [2,4-6], tyrosine phosphatase IA-2 (also known as ICA512) [7,11], and insulin [12]. Reliable and highly reproducible radioligand binding assays (RBA) have been developed for detecting these markers.

About 70% of type 1 diabetic patients have GAD markers (GADA) [6], whereas the percentage of positivity for the anti-IA-2 marker (IA-2A) is somewhat less [20]. The percentage of patients having at least one of these two markers is about 90% [15], making these tests very valuable tools for both basic research and practical medical intervention [14].

IA-2, a 106-kDa protein similar to members of the tyrosine-phosphatase family (PTPases), is a 979 amino-acids membrane protein with intracellular (C-terminal), extracellular (N-terminal), and transmembrane (residues 579-603) domains, and a 34-residue N-terminal signal sequence [21] (see FIG. 1). IA-2 is expressed in cells of the neuroendocrinal lineage as pituitary neurons and β cells of the pancreatic islet [22,23]. After various post-translational processing, including extensive proteolytic cleavage and glycosylation, IA-2 is transformed into several products with apparent molecular weights ranging 40 to 130 kDa [21]. In addition, the messenger RNA of IA-2 is spliced, generating a form that lacks the exon encoding for the transmembrane domain [24].

IA-2 lacks tyrosine-phosphatase activity [19]. However, it can be artificially rendered active by replacing residues Ala 877 and Asp 911 by Asp and Ala, respectively [25]. The lack of enzymic activity poses the question as to what is the biological function of the protein. To this respect, it was recently proven that IA-2-gene deficient mice have depressed insulin release in glucose tolerance tests [26].

Most IA-2 epitopes are located in the intracytoplasmic domain (residues 604 to 979) [27-29], which comprises the juxtamembrane area (residues 604-670) and the PTPase-like domain (residues 670-979). The most widely used antigen constructions for the detection of IA-2A are ICA512bdc (which includes residues 256-556 and 630-979, and which lacks amino-acids spanning 557 to 629 [30]), and IA-2ic (residues 604-979), which comprises the entire cytoplasmic portion [8]. Sensitivity of IA-21c for IA-2A detection is slightly higher than that of ICA512bdc, due to the absence in the latter of epitopes comprised in the juxta-membrane portion [24].

Because most IA-2A are directed against discontinuous epitopes [31], it is essential that the antigen used in the diagnostic test maintains its native conformation. Native IA-2ic has been produced in prokaryotic systems, as a fusion protein with, on the one hand, a N-terminal peptide that carries a biotinylatation site [32, 33] or, on the other, with glutation S-transferase (GST) [25,31]. The yield of properly folded IA-2ic using these constructions was very low; furthermore, antibody accessibility to the N-terminus of IA-2A might be compromised by the fusion with these rather large polipeptides.

There is therefore a need of practical methods for the large-scale production of autoantigens that would serve in the diagnosys of type 1 diabetes. The present invention fulfills this need by providing an inexpensive method of producing IA-2ic as a recombinant protein in *Escherichia coli* with high yield.

DESCRIPTION OF THE INVENTION

The present invention comprises novel nucleic acid molecules designed to improve the expression of IA-2ic, a fundamental antigen in autoimmune diabetes, necessary for IA-2 autoantibodies detection in prokaryotic systems.

In one aspect, the present invention refers to DNA molecules comprising optimized nucleotide sequences. The most important optimized sequences are SEQ ID NO:1, SEQ ID NO:2, SEQ ID NO:3, and parts of them.

As another object, the present invention provides a chimeric DNA molecule comprising any of the sequences SEQ ID NO:1, SEQ ID NO:2, SEQ ID NO:3, or parts of them, fused with sequences encoding an auxiliary peptide.

Also constitutes an object of the invention RNA molecules encoded by the optimized DNA molecules, either alone or fused to one or more auxiliary sequences.

In another object of the invention, expression vectors are provided that comprise the DNA molecules of the present invention. In them, the DNA molecules of the invention are within the context of one or more regulatory sequences that direct the expression of the IA-2ic antigen in bacterial cell. Preferably, the expression vectors provided are derived from the pET plasmid (Novagen).

A host cell transformed with DNA molecules like those of the present invention constitutes another object of the present invention. The transformed cell is preferably a prokaryotic cell and, particularly *Escherichia coli*.

Also constitutes another aspect of the present invention a method of producing IA-2ic comprising growing of cells transformed either by a DNA molecule like those of the invention, or by an expression vector like those of the invention, under suitable conditions for the production of said polypeptide. In a preferred embodiment, the transformed cells are of *Escherichia coli*.

The products encoded by the DNA molecules of the present invention and produced using the methods of the present invention are also part of the invention, as well as a procedure for in vitro diagnosis of autoimmune diabetes that comprises contacting a sample of the patient's body fluids with the product encoded by the DNA molecules of the invention. Finally, another object of the present invention is a diagnostic test for detecting autoimmune diabetes that comprises the product encoded by the DNA molecules of the invention.

DESCRIPTION OF THE FIGURES

FIG. 3 (B) shows a Western blot of whole lysate of bacteria expressing IA-2ic revealed with a pool of sera from IA-2A-positive patients. And FIG. 3(C) shows a Western blot of purified IA-2ic$H_6$, and IA-2ic(AD/DG)$H_6$ (lanes 1 and 2, respectively). In all panels, arrows indicate the electrophoretic mobility of ovoalbumin (43 kDa).

FIG. 8 is a listing of primers used during the cloning and mutagenesis processes carried out in the present invention.

DETAILED DESCRIPTION OF THE INVENTION

Figure 1:
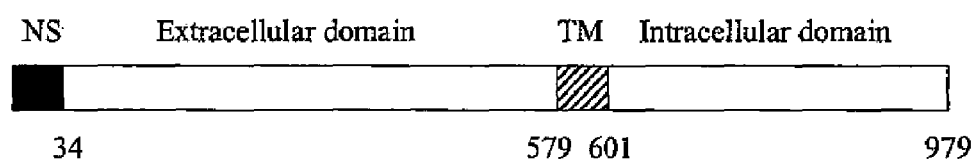
FIG. 1 schematically depicts the complete sequence of IA-2. The N-terminal sequence signal (NS) and transmembrane domain (TM) are highlighted.

In the description of the present invention a number of terms current in the field of genetic engineering are used. To facilitate understanding the scope of the present invention, some of these terms are defined below.

Within the context of the present invention, "optimized nucleotides sequence" refers to a nucleotides sequence from a gene that has been modified with the purpose of increasing the expression levels in a particular biological system.

The term "expression" refers to the production of a protein as a result of transcription of the gene encoding it in a messenger RNA molecule (mRNA), and its subsequent translation into a polypeptide chain. As known by experts in the art, the expression levels of genes are affected by regulatory elements (promoters, polyadenylation sites, etc.), and factors related to the aforementioned transcription and translation.

"tARN$^{AGG/Arg}$" refers to arginine transfer RNA that possesses a specific anticodon for the AGG codon.

"Regulatory sequences" refers to the sequences of nucleotides located before, after, or within the gene, which control the transcription and/or translation of the gene. Examples of regulatory sequences are promoters, transcription termination sequences, and polyadenylation sites.

The term "promoter" refers to the sequence of nucleotide (normally located before the 5' end of the gene reading frame) that regulates the gene transcription. These sequences are necessary to direct expression. As known by experts in the art, the position of a promoter with respect to the translation initiation site depends on the type of promoter, both in the case of natural ones as well as in those artificially added, and its efficacy to promote transcription depends on the presence of the molecules with which they interact.

"Chimeric DNA molecule" is a portion of DNA formed by the fusion of at least two DNA fragments, in an array previously nonexisting in nature. Whenever chimeric DNA molecules form a reading frame, proteins encoded by this type of molecule are called "fusion proteins" or "chimeric proteins".

The expression "operatively bound" refers to nucleotide sequences situated on a same nucleic acid molecule, which are associated in a way that the function of one is affected by the other. For example, a promoter is operatively bound to a gene when it is capable of affecting the expression of that gene, and means that this gene is under the transcriptional control of the promoter.

"Transfection" refers to the introduction of a DNA fragment carrying a functional gene, within an organism that previously lacked that gene.

"PCR" refers to the polymerase chain reaction.

"APP" refers to a peptide or protein auxiliary for expression and folding; these APP are used to express and/or purify proteins as fusion products.

"Primers" refers to polynucleotides necessary to initiate PCR.

Compared to previous attempts, the present invention comprises DNA molecules that allow an important increase in the production yield of IA-2ic. Since IA-2ic is a major antigen in autoimmune diabetes and is necessary for detection of autoantibodies against IA-2 (IA-2A), this invention also constitutes a contribution to the development of IA-2A detection techniques. Further, this invention provides DNA molecules with optimized nucleotide sequences encoding IA-2ic.

Figure 2:
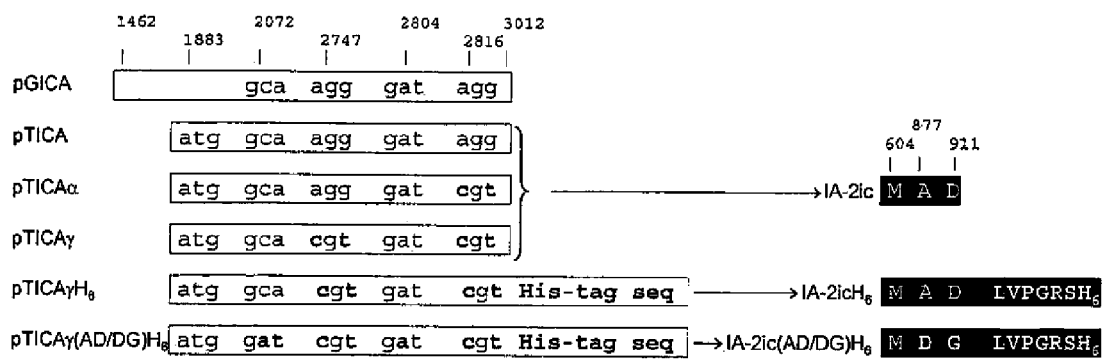
FIG. 2 is a schematic representation of IA-2ic encoding sequences and their predicted protein products. The names refer to the corresponding plasmid and encoded peptide, and the numbers refer to the base pair position in the complete IA-2 gene or to the amino-acid residue in the complete sequence of the IA-2 peptide.
Figure 3:
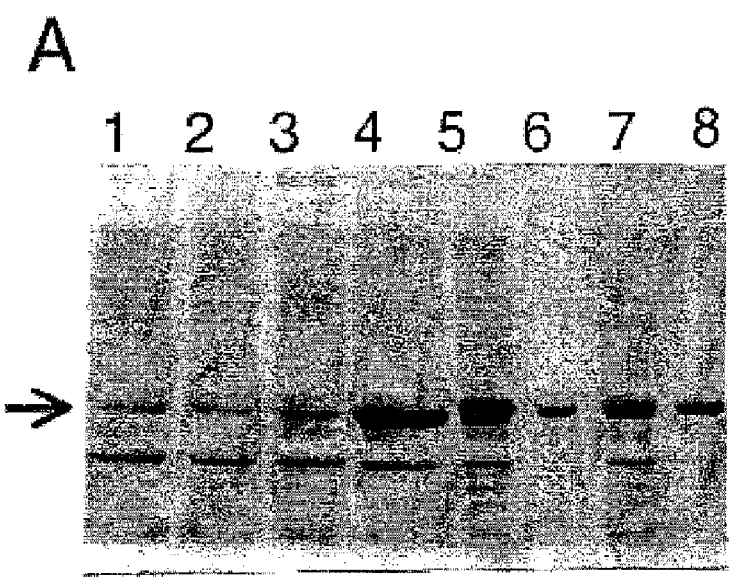
FIG. 3 (A) shows a SDS-PAGE revealing the expression level of IA-2ic encoded by pTICA (whole cell lysates before and after induction, lanes 1 and 2, respectively); IA-2ic encoded by pTICAα (whole cell lysates before and after induction, lanes 3 and 4, respectively); IA-2ic$H_6$ encoded by pTICAγ H6 (whole lysate of induced bacteria and purified product, lanes 5 and 6, respectively); and IA-2ic(AD/DG)$H_6$ encoded by pTICAγ (AD/DG)$H_6$ (whole lysate of induced bacteria and purified product, lanes 7 and 8, respectively).
Figure 3:
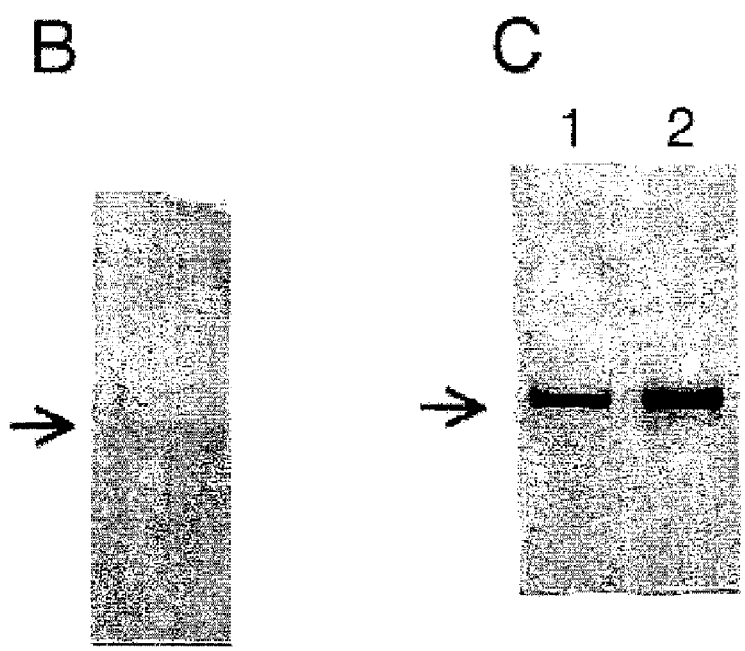

During the development of the present invention, when cells Escherichia coli were transformed with pTICA-a derivative of pET containing the natural encoding sequence for IA-2ic inserted in sites Nde I and BamH I, as shown in FIG. 2—the induced cultures showed extremely low. IA-2ic expression (FIG. 3 A, lanes 1 and 2). These results confirmed prior reports on the expression of IA-2ic [33]. When analizing the nucleotide sequence of the IA-2ic gene, two AGG codons were found starting, respectively, at positions 2747 and 2816, according to the numbering of the base pairs in the complete IA-2 gene reported in [9] (SEQ ID NO:4), which have low frequency of use in *Escherichia coli*, as defined in [34,35]. Thus, translation of the natural IA-2ic gene may have been hindered by insufficient quantities of TARN$^{AGG/}$$_{Arg}$.

Degeneracy of the genetic code enables a single amino-acid to be encoded by more than one codon. For example, six different codons encode serine, and four different codons do so for alanine. However, the frequency of use of the codons for each amino-acid varies according to the group of organisms involved. When comparing the usage frequency distribution of codons characterizing different organisms, it is observed that as the organisms are less phylogenetically related, they will differ more in the usage frequency of codons for the different amino-acids.

Apparently, these differences in the usage frequency of codons affect the expression levels of genes by regulating the elongation rate of peptides. This argument is supported by two lines of experimental evidence. First, the rate of polypeptide synthesis depends on the nature of the codons being translated, as well as the initial kinetics for the formation of the ternary complex of transfer RNA (tRNA). Secondly, the frequency distribution of codons in the cell tRNA tends to follow the frequency distribution of codons in mRNA. In this way, when a heterologous gene from a very phylogenetically distant species is inserted into a cell, the differences in the usage frequency of alternative codons may lead to a significant waste of the cell's expression capacity. It follows then that using optimized nucleotide sequences— in which the frequencies of codons reflect those frequencies found naturally in the host organism—is useful and advantageous for high-level expression of recombinant proteins.

Nevertheless, the genetic expression does not depend solely on the coding nucleotide sequences, but also on various types of interactions between defined portions of DNA and proteins (in turn encoded by other genes), and on various feedback mechanisms within and between cells. A typical eukaryotic gene consists of different, operationally distinguishable portions (exons and introns, promoters, enhancers, and other control elements), so constituting a complex system of hardly predictable behavior when attempting expression outside its natural context.

Degeneracy of the genetic code, as already mentioned, is a phenomenon whereby various codons (commonly known as alternative codons) encode to a same amino-acid. This allows introducing variations in the nucleotide sequence of a gene without modifying the amino-acid sequence of the expressed polypeptide. Said variations (called silent mutations) may affect the stability of the mRNA and the tendency of the mRNA to form secondary structures in segments important for translation initiation, finally affecting the expression level of the polypeptide encoded by the gene. On the other hand, despite that alternative codons specify the same amino-acid, these are not equally used. As a result of this difference in use of the alternative codons, translation of the mRNA is slower in those mRNA zones where less-frequently-used codons are more abundant, whereas where those frequently-used are more abundant, translation is faster. This differential use varies for each species, with the level of use of each of the alternative codons being known for many species.

Despite knowing the level of use of alternative codons in many biological systems, replacing less-frequently-used ones with those frequently-used does not assure an increased expression of the encoded polypeptide. This is due in part to the contribution of other factors like the aforementioned mechanisms of interaction. It is also necessary to take into account that pause in the translation produced by several less-frequently-used codons is a non-additive phenomenon, which may mean that replacing just one of these codons may have no appreciable effect on the expression rate of the polypeptide. In fact, in the case of the present invention, replaced codons were not the only ones less-frequently-used, although they were the ones of lowest usage among those in this category. Moreover, it was observed that the presence of less-frequently-used codons in the mRNA sequence fulfills a physiologic function, facilitating folding of the growing polypeptide; so that the replacement of a less-frequently-used codon by a frequently-used may disturb the folding of the protein and, consequently, its expression in the soluble form.

On the other hand, it is important to mention that, in the case of the present invention, the encoded polypeptide is a fragment of a protein (spanning amino-acids 604 to 979). Because of the lack, to date, of structural studies on this polypeptide, the possibility that the selected portion of protein were unable to fold autonomously could not be discarded in advance. If this occurred, the appearance of the correctly-folded polypeptide in solution could be an energetically unfavorable event, which could be the cause of the low yield of previous attempts [33]. The true magnitude of this problem can be appreciated considering the numerous cases in which the absence or addition of a few amino-acids in the N- or C-terminal ends of a polypeptide are crucial for the overall folding of the protein and its solubility.

Finally, the expression level of a protein may be affected by the conditions under which the biological system is developed as, for example, those of the culture medium (temperature, induction time, presence of certain nutrients), that have little or nothing to do with the nucleotides sequence of the gene.

Therefore, despite that inspection of the sequence of nucleotides that encode IA-2ic revealed the presence of less-frequently-used codons, it was not possible to predict, without further research, that their replacement by frequently-used codons would improve expression.

This invention provides DNA molecules with nucleotide sequences that encode IA-2ic wherein the natural, less-frequently-used in bacteria AGG codons, were replaced by CGT codons which are frequently-used in *Escherichia coli* [34,35] (TABLE 1). As a result, the present invention includes DNA molecules that comprise the following optimized sequences: SEQ ID NO:1, a nucleotide sequence that encodes IA-2ic, wherein both natural codons have been replaced; SEQ ID NO:2, which encodes IA-2ic and wherein the only one replaced is codon AGG starting at position 2747 (the numbers correspond to the base pair position in the complete IA-2 gene—SEQ ID NO:4—reported in [9]); and SEQ ID NO:3 in which only codon AGG starting at position 2816 was replaced; and nucleotide sequences with at least 50% of identity with those, in which at least one of the codons initiating at positions 2747 and 2816 is CGT.

TABLE 1

Frequency of usage of Arg coding triplets in *Escherichia coli*

| Triplet | CGT | CGC | CGA | CGG | AGA | AGG |
|---|---|---|---|---|---|---|
| Frequency[a] | 20.7 | 21.1 | 3.7 | 5.7 | 2.7 | 1.6 |

[a]In number of occurrences per thousand.

These replacements introduce no changes in the amino-acid sequence of IA-2ic, but, as has been demonstrated, they lead to an important increment in the protein expression levels when those sequences are used to produce IA-2ic, for example, in *Escherichia coli*. For instance, experiments yielded 80 mg of protein per liter of culture, whereas with the native gene, the amount of protein was not quantifiable by SDS-PAGE; at the same time, prior attempts published by other research groups [36] reported yields of 1 mg of protein per liter of culture using the native gene secuence. In addition, in Western blot assays, RIA and ELISA, the antigen obtained by the method of the invention was able to bind to anti-IA-2 specific antibodies, either from immunized animals or from patients sera samples, proving to be fully reactive from an immunological point of view.

To facilitate the purification procedures of IA-2ic peptides encoded by the optimized molecules of the present invention, chimeric DNA molecules were developed, which are also part of the present invention. In the latter, the 3'-end of the optimized DNA molecules encoding IA-2ic is linked with sequences encoding an APP. The addition of the APP does not affect the high expression yield achieved by optimizing the IA-2ic gene sequence. A preferred APP for use in these chimeric DNA molecules is a His-tag (frequently referred to as $H_6$). Once expressed in an adequate biological system, the chimeric genes of this invention allow obtaining fusion proteins formed by a IA-2ic antigen bound to an APP (for example, His-tag), which may be easily purified through chromatographic methods. The fusion proteins obtained in this way keep their immunochemical properties intact.

Sequences encoding APP may be linked to the 3'-end of optimized nucleotide sequences encoding to IA-2ic previously cloned in a plasmid. Therefore, another object of the present invention is an expression vector containing an optimized nucleotide sequence that encodes IA-2ic antigene. Said expression vectors may further comprise one or more operatively-bound regulatory sequences directing the expression of the encoded product in a bacterial cell. In addition, said vectors may contain a sequence that encodes an APP bound to one of the ends (in this case, 3') of the nucleotides sequence that encodes IA-2ic. These vectors are evidently useful for the transfection of cells, which, once modified, will produce, under appropriate suitable culture conditions, the IA-2ic peptides, alone or bound to APP. In one of its preferred embodiements, the vector is a plasmid derived from the pET plasmid, which is commercially available and possesses the promoter of bacteriophage T7 RNA polymerase. These plasmids are particuolarly suitable for the transformation of bacterial cells. They are particularly useful for transfecting *Escherichia coli* cells.

All the genetic constructions of the present invention may be prepared by techniques and procedures well known to those expert in the art. For example, both DNA and RNA useful for the production of proteins, may be synthesized by methods involving biological systems. For DNA, cloning the gene in a plasmid capable of autonomous replication inside bacteria, is an example of a method for obtaining a good quantity of specific DNA. To obtain specific RNA in vitro, a DNA molecule—which must contain the sequence that it is desired to transcribe along with the necessary regulatory sequences—is incubated in a medium containing the biosynthetic apparatus necessary to synthesize RNA. This biosynthetic apparatus is generally found in commercial systems like rabbit reticulocyte lysates [53], or wheat germ extracts [54]. Subsequent to obtaining RNA and DNA molecules of native secuences, the optimized sequence may be obtained, for example, through directed mutagenesis. The DNA and RNA constructions may be optionally obtained by chemical synthesis, through in vitro assembly of the constituent nucleotides. This procedure may be carried out manually using well-established techniques [55], or through automated chemical synthesis using one of the several commercially available instruments.

A further aspect of this invention is a transformed host cell containing a DNA molecule that comprises an optimized nucleotide sequence encoding IA-2ic antigen. Since the DNA molecules of the present invention were optimized for expressing IA-2ic in prokaryotic systems, the host cells are preferably bacterial cells. Among the different bacterial cells, *Escherichia coli* cells are preferred.

The transformed cells of the present invention may be obtained by methods well-known to the expert in the art. For examOple, DNA sequences of the present invention may be introduced into host cells using vectors. Although the vectors are preferably plasmids, any other type of vector can be used as, for example, bacteriophages, cosmids, phagemids, YACs, etc. The use of vectors may be avoided resorting to transformation of cells by direct insertion of the IA-2ic gene of the present invention into the cell genome, preferably a bacterial cell. Another transformation procedure that allows omitting the use of vectors consists of obtaining the mRNA (by isolation or chemical synthesis), aOnd incubating it with an intracellular bacterial extract, thus expressing the protein in vitro. Therefore, mRNA molecules derived from transcription of the optimized DNA sequences is another aspect of the invention, as well as chimeric DNA molecules provided through this invention.

Another aspect of the present invention is a method of preparing IA-2ic by culturing under appropriate conditions, cells transformed with the DNA molecules of the present invention. Once the peptides have been expressed, they can be purified (for example, by chelated-metal affinity chromatography [37]) for their subsequent use in the diagnosis of autoimmune diabetes. Consequently, both the polypeptides produced by preparing IA-2ic of the present invention, and the in vitro diagnostic procedures employing them (in which a sample of the patient's serum, plasma or blood is contacted with the polypeptide) are part of the present invention. Finally, another aspect of the present invention is a diagnostic ki0t for detecting autoimmune diabetes that comprises the polypeptide of the invention.

The following examples are presented to clarify the nature of the present invention. Their purpose is to illustrate the development and application of the invention, and should not be considered as limiting its scope.

EXAMPLE 1

Obtaining DNA Constructions

Total RNA was obtained by extraction with phenol-chloroform [38] from human pancreas samples obtained for diagnostic or surgical purposes. Single-strand DNA was prepared by reverse transcription using primer icaR (FIG. 8) and reverse transcriptase of the Moloney leukemia virus (Promega, Madison, USA). The previous reaction product was subjected to PCR [39] with primers icaR and icaF using Taq polymerase (Promega). As a result, a DNA molecule was obtained spanning position 1462 to position 3095 of the complete IA-2 gene [40]. This molecule was cloned in a pGEM-T Easy plasmid (Promega) generating pG-ICA (FIG. 2).

Using pG-ICA, a DNA fragment of 1627 base pairs (bp) was amplified by PCR with primers icNde and 3095BamHI, using Pfu DNA polymerase (Promega) in the PCR. The product was cloned in pGEM3zf (Promega) previously digested with Sma I. A fragment of 1215 bp was excised from the resulting plasmid with Nde I and BamH I, which was cloned in a pET9b plasmid (Novagen), generating plasmid pTICA.

Subsequent derivatives of pTICA (SEQ ID NO: 4), described in FIG. 2, were generated by directed mutagenesis. To generate pTICAα (SEQ ID NO:3) (FIG. 2), a DNA fragment was amplified by PCR using pTICA and primers 2797c and 3095BamHI. The product was digested with Pst I and Nco I, and cloned at the sames sites as pTICA. To generate pTICAγ (SEQ ID NO: 1), two PCR were carried out using pTICAα as a template with pairs of primers 2741cF-3095BamHI and 2741cR-icNde. The products underwent another PCR with primers icNde and 3095BamH, generating a fragment, which, once digested with Pst I and Nco I, was cloned at the sames sites as pTICAα. To add the sequence encoding the His-tag, a PCR was carried out with primers icNde and 3'THisBam using pTICAα as the template. The product was digested with Pst I and BamH I, and cloned at the same sites as pTICAα and pTICAγ, thus resulting in plasmids pTICAαCH$_6$ and pTICAγH$_6$ (SEQ ID NO:1), respectively (for simplicity, FIG. 2 shows only pTICAγH$_6$ and its derivative). To generate the amino-acid mutations, PCR was carried out on pTICAγH$_6$ using primers 2797cDG and 3'THisBam. The product was digested with Pst I and BamH I, and cloned at the same sites as pTICAγ, thus resulting in plasmid pTICAγ(DG)H$_6$ (not shown in FIG. 2). Using this plasmid as a template, a new PCR was carried out with primers A877D and 3'THisBam, and the product was digested with Pvu II and BamH I and cloned at the same sites as pTICAγ(DG)H$_6$, thus resulting in plasmid pTICAγ(AD/DG)H$_6$ (SEQ ID NO:16).

All the DNA sequences encoding IA-2 or its variants, were confirmed by sequencing (DNA Sequencing Facility of the Cancer Research Center, University of Chicago, USA).

EXAMPLE 2

Synthesis and Purification of IA-2ic and its Variants

BL21 (DE3)$_p$LysS *Escherichia coli* bacteria transformed with plasmids pTICA, pTICAα, pTICAγH$_6$, or pTICAγ(AD/DG)H$_6$, were grown at 37° C. in Luria-Bertani (LB) nutrient medium (100-200 mL), supplemented with 50 pg/mL kanamycin and 34 μg/mL chloramphenicol to A$_{600}$ $_{nm}$=1. Protein expression was induced for about 16 h at 20° C. with 10 mM IPTG (Fluka). After induction, the bacteria were collected by centrifugation and resuspended in 10 mL of lysis buffer (50 mM sodium phosphate, 300 mM NaCl, pH 6.5), supplemented with 10 mM PMSF (Sigma, St. Louis, Mo.), and lysed by compression-decompression with a french press (Spectronics Instruments, Inc., NY). The soluble fraction of the lysate was isolated by centrifugation (12000 g, 15 min, 4° C.). If dealing with a variant of IA-2ic containing His-tag, the soluble fraction was supplemented with 10 mM imidazole, pH 6.5, and was mixed with 2 mL of agarose Ni-NTA (QIAGEN) preequilibrated with the same solution. After incubating for 1 h at 4° C., the suspension was poured into a 1.5 cm×5.0 cm column and washed five times with a lysis buffer containing 40 mM imidazole, pH 6.5. Then, matrix-bound protein was eluted with lysis buffer containing 200 mM imidazole, pH 6.5. Finally, the solution with which the protein was eluted was exchanged to 50 mM sodium phosphate, pH 6.5, or 50 mM MES, pH 6.5 by dialysis for 20 h at 4° C. When a greater purity was required, proteins were purified by ion-exchange chromatography in a FPLC system (Pharmacia-LKB Biotechnology). In this case the solution used was 30 mM HEPES, pH 6.5 and the samples were loaded into a MonoQ HR 5/5 column (Pharmacia-LKB Biotechnology), from which the protein was eluted with an increasing ionic-strength gradient to 30 mM HEPES, pH 6.5, 500 mM NaCl.

EXAMPLE 3

Assessment of the Expression Level by SDS-PAGE

Protein samples were first denatured at 100° C. for 5 min in a buffer solution containing 1% sodium dodecyl sulfate, 4% β-mercaptoethanol, 0.25% bromophenol blue, 0.3 M Tris CIH, pH 6.8. Then 10-20 μL were placed in each of the lanes located at the upper edge of a discontinuous gel of 10% polyacrylamide as described in [41]. These were then subjected to a 30 mA current for a time whereby the bromophenol reached the bottom edge of the gel (2-3 h). Finally, the proteins present in the gel were dyed with 0.5% Coomasie brilliant blue R250 in an aqueous solution of 50% methanol, 10% acetic acid. The results are shown in FIG. 3A.

EXAMPLE 4

Immunoreactivity Analysis by Western Blot

Unstained SDS-PAGE gels obtained as in the prior example were contacted with nitrocellulose membranes. The proteins contained in the gel were transferred to the membrane by a 100 mA cross current. Then, the membrane was separated and incubated with a blocking solution (2% dessicated low-fat milk in 50 mM sodium phosphate, 125 mM NaCl, pH 6.5 for 2 h). This membrane was then incubated for 2 h with a specific anti-IA-2ic rabbit antibody in incubation solution (blocking solution, 0.5% Tween 20). The membrane was then incubated with rabbit immunoglobulins specific mouse antibodies conjugated to horseradish peroxidase, diluted 1/1000 in incubation solution. This was then incubated with a solution of 0.3% α-chloronaphthol in 10% methanol and in the presence of H$_2$O$_2$ until visualization of the bands. Between incubations, five washes with 50 mM sodium phosphate, 125 mM NaCl, 0.5% Tween 20, pH 6.5, were always carried out. The results are shown in FIG. 3 B-C, and indicate the immunoreactivity of variants IA-2icH$_6$ and IA-2ic(AD/DG)H$_6$.

EXAMPLE 5

Immunoreactivity Analysis by RIA and ELISA

Radioimmunoassays (RIA) were carried out in 60 μL of solution containing about 10000 dpm of [$^{35}$S]IA-2ic and different concentrations (from 50 to 3000 nM) of IA-2ic (in a soluble fraction of bacterial lysate), pure IA-2icH$_6$, or pure IA-2ic(AD/DG)H$_6$, and aliquotes of an anti-IA-2ic specific polyclonal rabbit serum in buffer solution for RIA (50 mM sodium phosphate, 150 mM NaCl, pH 6.5, 0.05% Tween 20, 1 mg/mL bovine seroalbumin). Following one-week incubation at 4° C., 50 μL of a 50% suspension of protein A-Sepharose 4B FF (Sigma, St. Louis, Mo.) were added to a buffer solution for RIA, and this was incubated for 2 h at 4° C. in an end-over-end shaker. After sedimentation, protein A-Sepharose was washed twice with buffer solution for RIA containing 0.35 M NaCl and resuspended in 100 μL of 1% sodium dodecylsulfate. The supernatants of each reaction were transferred to appropriate vials to quantify the radioactivity in a liquid scintillation counter. The results were adjusted by least squares method to the following general equation:

$$\frac{b}{f} = \frac{a}{1+cF} \quad (1)$$

where b and f refer to the radioactive antigen (tracer bound and free, respectively). F refers to the total "free" antigen, and a and c are auxiliary parameters. From the adjusted curve an average affinity constant $K_{app}$ was derivedved, which may be calculated as 1/(concentration of non-radioactive antigen) at the value of b/f=0.5 [42]. The results, shown in TABLE 2 and in FIG. 4 demonstrate that the variants of IA-2ic of the present invention bind to specific antibodies.

TABLE 2

RIA assessment of IA-2ic variants affinity for a specific polyclonal rabbit serum[a].

| Variant | $K_{app} \times 10^8 (M^{-1})$[b] |
|---|---|
| IA-2ic | 2.2 (1.3–3.6) |
| IA-2icH$_6$ | 4.2 (1.9–9.2) |
| IA-2ic(AD/DG)H$_6$ | 4.2 (1.7–10.0) |

Figure 4:
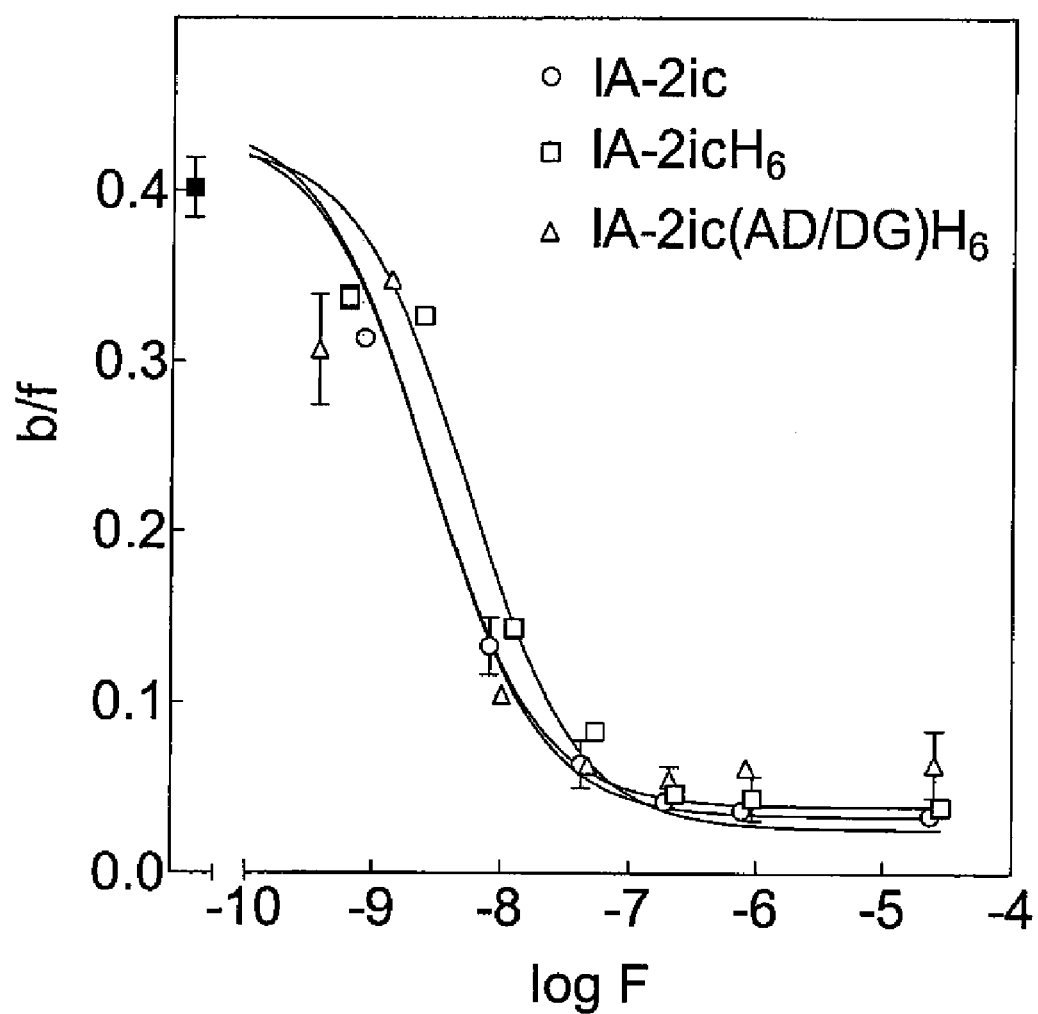
FIG. 4 shows the results of a radioimmunoassay (RIA) using different concentrations of IA-2ic variants against a radioactive tracer [$^{35}$S] IA-2ic. The tracer was incubated with an IA-2ic specific rabbit polyclonal serum and different concentrations of each of the IA-2ic variants. The ratio of bound-to-free (b/f) [$^{35}$S] IA-2ic as a function of the logarithm of the molar concentration of free antigen (F) was plotted in a coordinates system. The solid square represents b/f in the absence of unlabeled antigen. IA-2ic$H_6$ and IA-2ic(AD/DG)$H_6$ concentrations in solution were calculated based on the absorbance at 280 nm. The concentration of IA-2ic in crude extract was estimated by SDS-PAGE densitometry, using a calibration curve obtained with known concentrations of IA-2ic$H_6$. $K_{app}$ for each variant are summarized in TABLE 2.

[a]Displacement data are shown in FIG. 4. [b]$K_{app}$ values were calculated as described in [42] and 95% confidence intervals are shown in parenthesis.

In addition, by carrying out an ELISA, the recombinant antigens obtained through the present invention proved useful as diagnostic aid in autoimmune diabetes. Since the preliminary results with conventional single-well tests suffered from unacceptably high unspecific signal, an assay format was developed, which we call bcELISA (Blank-Corrected ELISA), where the nonspecific signal is subtracted from the final color development. The percentages of positivity for the bcELISA and the radioligand binding assay (RBA) were 54 and 62% respectively, while none of the techniques gave positive values among the control group (see TABLE 3).

Figure 7:
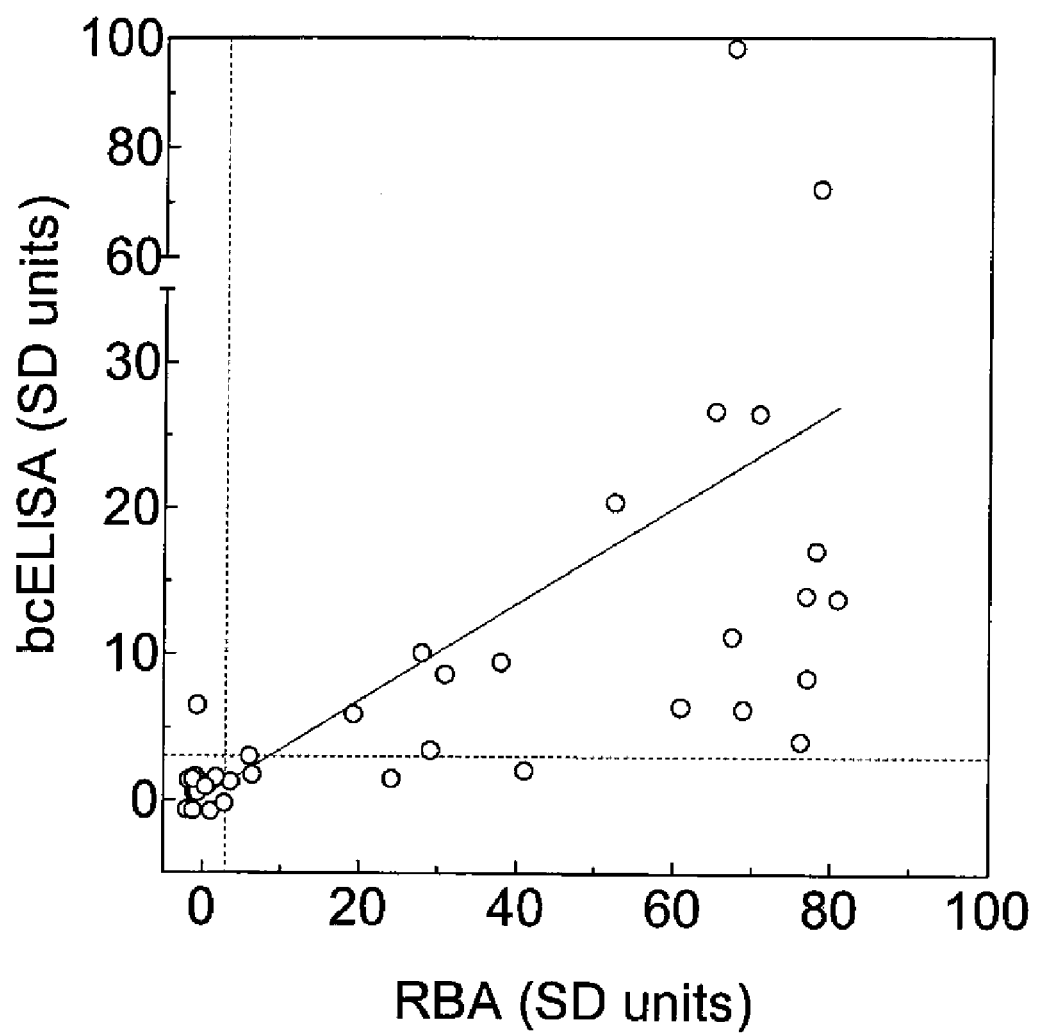
FIG. 7 shows the correlation between between bcELISA enzimoimmunoassay and the radioligand binding assay (RBA). Signals are expressed as standard deviation units (SD units). Statistical parameters were r=0.53 and P<0.001. The linear regression line is shown. Control patients' data were not included in the graph, and all points correspond to patients' sera.

It is worth mentioning that the results of the bcELISA were similar to those of the best ELISA published previously [13,52]. Sera from 4 of 32 patients were positive by RBA and negative by bcELISA. Inversely, the bcELISA detected IA-2A in one negative RBA patient. The correlation between bcELISA and RBA was significant (r=0.53, P<0.001; TABLE 3 and FIG. 7). However, the slope of the regression line differed from the unit, reflecting differences between the principles of both techniques [42,43]. Further, the conformation of the immobilized and chemically-modified antigen in ELISA may differ from the soluble radioactive antigen in RBA. Therefore, ELISA and RBA methods do not usually show comparable values for each patient, and the results may only be judged by the overall agreement in total positivity.

TABLE 3

Analysis of IA-2A of sera from diabetic patients[a]

|  | n | RBA + | RBA − | bcELISA + | bcELISA − |
|---|---|---|---|---|---|
| Patients | 37 | 23 (62) | 14 (38) | 20 (54) | 17 (46) |
| Controls | 30 | 0 | 30 (100) | 0 | 30 (100) |

[a]The reference RBA was carried out as described earlier [44, 45], using [$^{35}$S]IA-2ic sinthesized in vitro.
The bcELISA was carried out with biotinylated ia-2icH$_6$
Percentages are in parentheses.
The two methods showed no significant differences in detecting positive samples (Z = 0.706, P = 0.24).

ELISA formats are relatively inexpensive and may be executed by technicians in simply equipped hospital laboratories. ELISA require no radioactive material. On the contrary, RBA is the kind of assay that is carried out in well-equipped research or diagnostic centers, is expensive, and requires highly skilled personnel and radioactive materials disposal service. With these considerations in mind, and even if in a larger study it were slightly less sensitive than RBA, the performance of bcELISA in detecting IA-2A can be judged as satisfactory, thus the new method holds great promise for large scale screening of samples in preventive medicine.

EXAMPLE 6

Analysis of the Convormation by Circular Dichroism Spectroscopy

Figure 5:
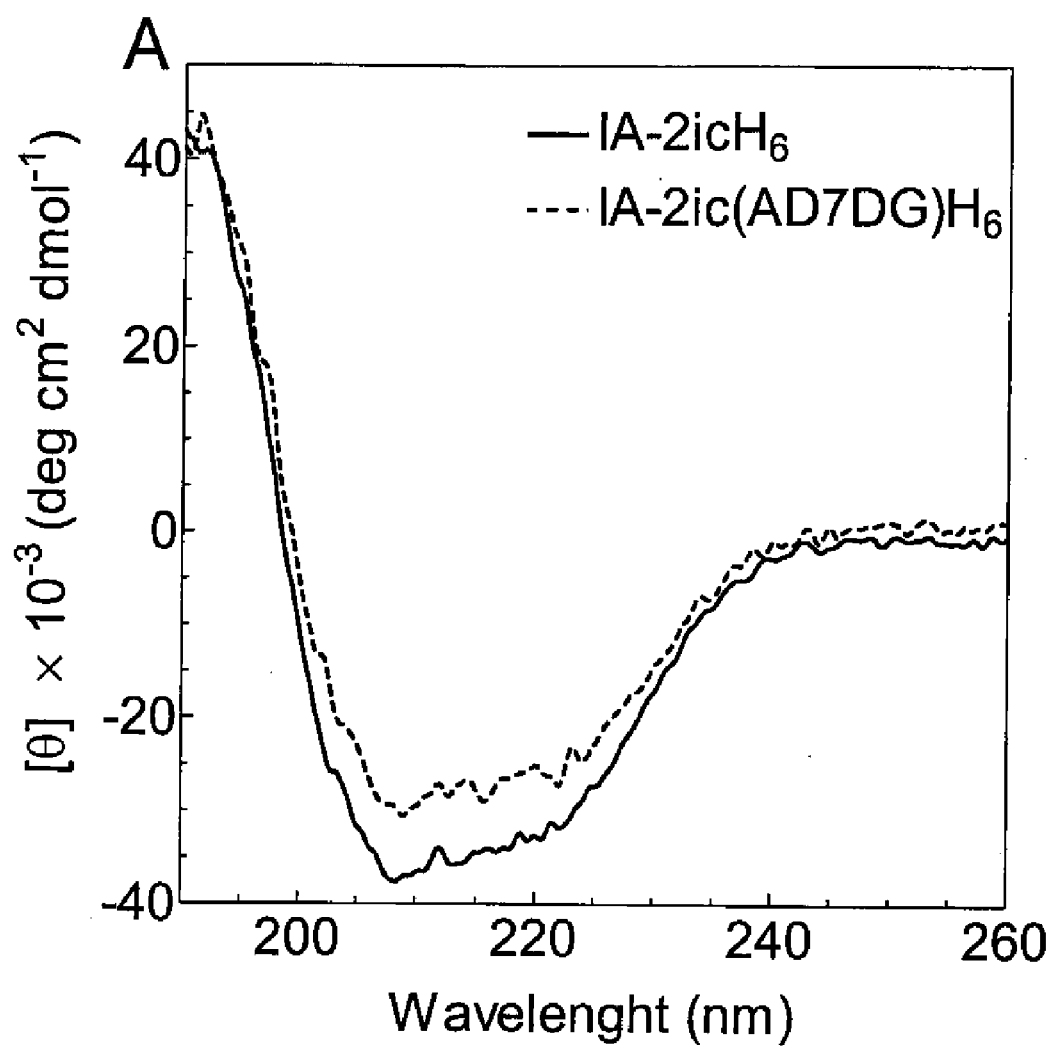
FIG. 5 shows some representative spectra of circular dichroism in the far-UV (A) and near-UV (B) spectra of IA-2ic$H_6$ and IA-2ic(AD/DG)$H_6$. Protein concentration was 0.7 μM (far UV spectrum) or 10 μM (near-UV spectrum). In both cases, the proteins were dissolved in 50 mM sodium phosphate, 200 mM NaF, pH 6.5.
Figure 5:
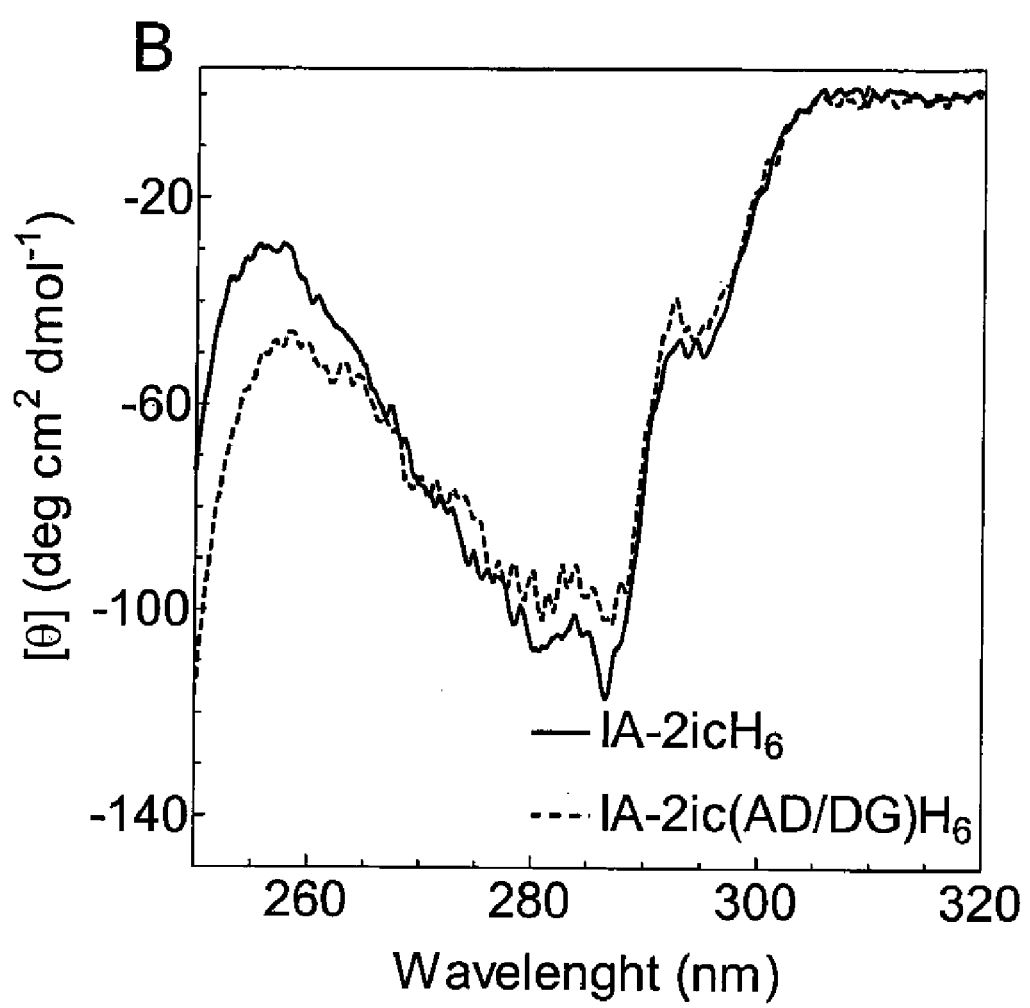

The appropriate conformation of the His-tag containing variants of IA-2ic of this invention was confirmed by circular dichroism spectroscopy. The Circular Dichroism Spectroscopy measurements were carried out at 20° C. on a Jasco 810 spectropolarimeter (Jasco Corporation, Japan) equipped with a peltier-effect device for temperature control. The instrument was calibrated with (+) 10-camphorsulfonic acid following the manufacturer's instructions. Scan speed was set to 20 and 50 nm/min (for near UV and far UV, respectively) with a 1-s response time and 1-nm bandwidth. Measurements in the near-UV were carried out in 1-cm cells containing protein in a concentration of 10-12 μM in 50 mM sodium phosphate, pH 6.5. On their part, 1-cm cells were used for the far-UV, containing protein concentration of 0.6-0.8 mM in 2.6 mM sodium phosphate, 200 mM NaF, pH 6.5. Six spectra were recorded and averaged for each sample and are presented smoothed with a fourth-degree 10-point-moving-window polynomial Savizky-Golay filler [46]. The figures show the representative trace of at least two measurements from different protein preparations. The far-UV results (shown in FIG. 5A) indicated that both variants of IA-2ic are similar in secondary structure, with a predominantly α-helix spectrum. This agrees with the three-dimensional structure expected, assuming the structural similarity with other homologous tyrosine phosphatases characterized by X-ray crystallography [47-49]. In the near-UV, the spectra were strong and rich in structure (FIG. 5B). Similar and well-defined negative bands of Trp and Tyr indicated that these aromatic groups are located in highly asymmetrical environments, thus providing evidence in favor of a nearly identical conformation of both variants.

EXAMPLE 7

Size-Exclusion Chromatography

Figure 6:
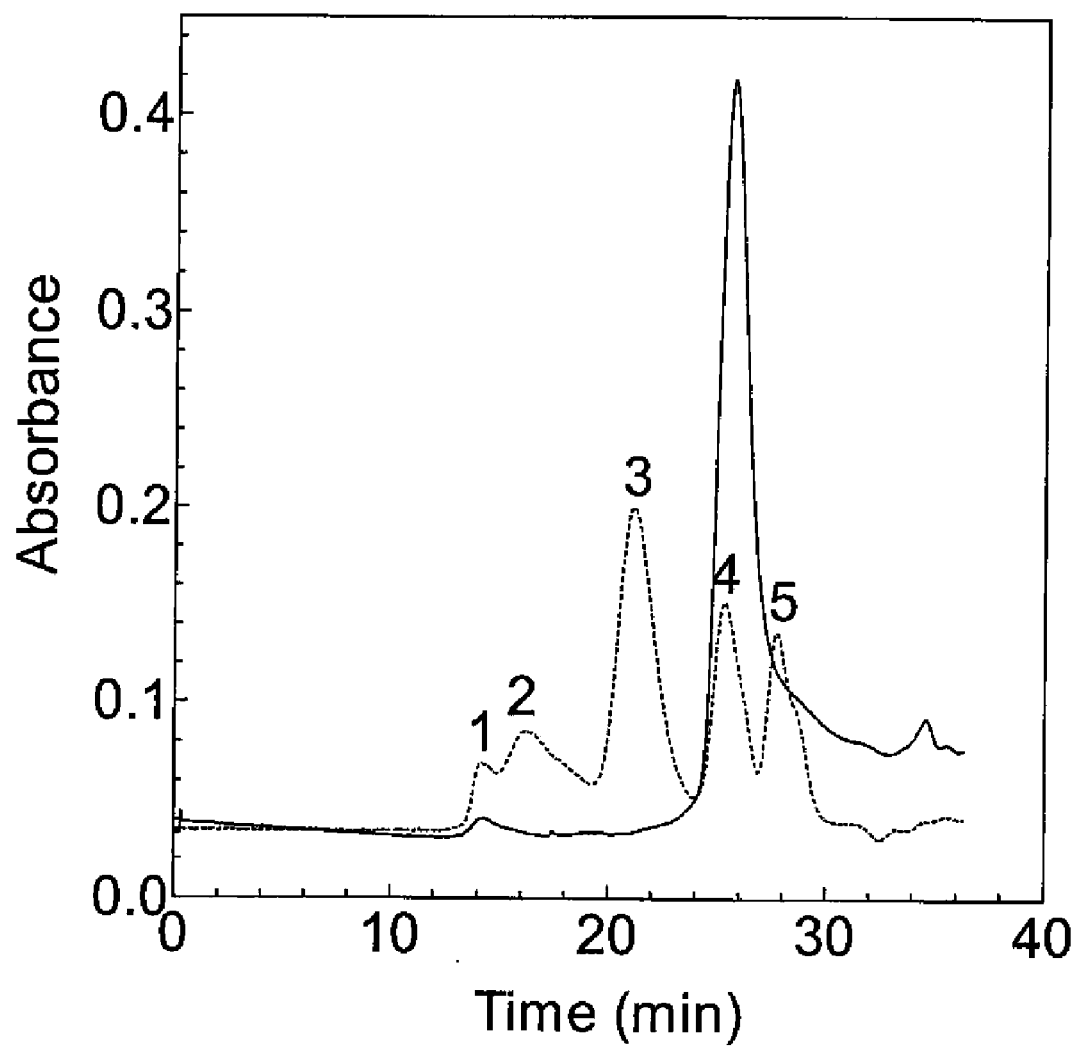
FIG. 6 shows a scheme of a size-exclusion chromatography of IA-2ic$H_6$ (solid line) and reference proteins (dotted line). Peaks 1-5 correspond to thyroglobulin (670 kDa), bovine IgG (158 kDa), ovoalbumin (44 kDa), myoglobin, and vitamin B12(1.3 kDa) (17 kDa), respectively.

Hydrodynamic dimensions and protein aggregation state were determined by size-exclusion chromatography in a FPLC system equipped with a Superose 12 column (Pharmacia-LKB Biotechnology), using 100 mM sodium phosphate, pH 6.5, as elution solution. The hydrodynamic volume was calculated by comparison with proteins of a known size as indicated in FIG. 6. The results were consistent with an adequately folded, monomeric state.

EXAMPLE 8

Controlled Digestion with Trypsin

IA-2icH$_6$ in a 30 mM concentration was incubated with trypsin in a 100:1 weight of protein-to-protease ratio in 50 mM sodium phosphate, pH 6.5 at 37° C. or 4° C. Samples were withdrawn at different times and analyzed by SDS-PAGE. At 4° C., the digestion produced two principal fragments of about 40 and 38 kDa. Treatment at 37° C. resulted in complete digestion. There are reports of hot proteolytic points in this protein. IA-2 forms in vivo a product of 40 kDa by specific proteolysis at the N-terminus [24,50] In cell-free extract, the principal proteolytic product was a few residues shorter [51]. Thus, IA-2icH$_6$ expressed in *Escherichia coli* seems to present in vitro the same protease susceptible nicking points as in vivo, which constitut es additional evidence in support of its conformational integrity.

CITED REFERENCES

[1] Castaño, L. and Eisenbarth, G. S. (1990) Annu. Rev. Immunol. 8, 647-679.
[2] Beekkeskov, S., Aanstoot, H. J., Christgau, S., Reetz, A., Solimena, M., Cascalho, M., Folli, F., Richter-Olesen, H. and De Camilli, P. (1990) Nature 347,151-156.
[3] Maclaren, N., Schatz, D., Drash, A. and Grave, G. (1989) Diabetes 38, 534-538.
[4] Lernmark, A. (1999) Clin. Chem. 45, 1331-1338.
[5] Richter, W., Endl, J., Eiermann, T. H., Brandt, M., Kientsch-Engel, R., Thivolet, C., Jungfer, H. and Scherbaum, W. A. (1992) Proc. Natl. Acad. Sci. USA 89, 8467-8471.
[6] Atkinson, M. A., Kaufman, D. L., Newman, D., Tobin, A. J. and Maclaren, N. K. (1993) J. Clin. Invest. 91, 350-356.
[7] Rabin, D. U., Pleasic, S. M., Palmer Crocker, R. and Shapiro, J. A. (1992) Diabetes 41,183-186.
[8] Rabin, D. U., Pleasic, S. M., Shapiro, J. A., Yoo Warren, H., Oles, J., Hicks, J. M., Goldstein, D. E. and Rae, P. M. (1994) J Immunol 152, 3183-3188.
[9] Lan, M. S., Lu, J., Goto, Y. and Notkins, A. L. (1994) DNA Cell. Biol. 13, 505-514.
[10] Bonifacio, E., Boitard, C., Gleichmann, H., Shaftock, M. A., Molenaar, J. L. and Bottazzo, G. F. (1990) Diabetologia 33, 731-736.
[11] Myers, M. A., Rabin, D. U. and Rowley, M. J. (1995) Diabetes 44,1290-1295
[12] Palmer, J. P., Asplin, C. M., Clemons, P., Lyen, K., Tatpati, O., Raghu, P. K. and Paquette, T. L. (1983) Science 222, 1337-1339.
[13] Verge, C. F., Gianani, R., Kawasaki, E., Yu, L., Pietropaolo, M., Jackson, R. A., Chase, H. P. and Eisenbarth, G. S. (1996) Diabetes 45, 926-933.
[14] Bingley, P. J., Christie, M. R., Bonifacio, E., Bonfanti, R., Shattock, M., Fonte, M. T., Boftazzo, G. F. and Gale, E. A. (1994) Diabetes 43,1304-1310.
[15] Bingley, P. J., Bonifacio, E., Williams, A. J., Genovese, S., Bottazzo, G. F. and Gale, E. A. (1997) Diabetes 46,1701-1710.
[16] Seissler, J., Morgenthaler, N. G., Achenbach, P., Lampeter, E. F., Glawe, D., Payton, M., Christie, M. and Scherbaum, W. A. (1996) Diabetologia 39, 1351-1356.
[17] Borg, H., Fernlund, P. and Sundkvist, G. (1997) Clin. Chem. 43, 2358-2363.
[18] Christie, M. R., Roll, U., Payton, M. A., Hatfield, E. C. and Ziegler, A. G. (1997) Diabetes Care 20, 965-970.
[19] Kulmala, P., Savola, K., Petersen, J. S., Vähäsalo, P., Karjalainen, J., Löppönen, T., Dyrberg, T., Akerblom, H. K. and Knip, M. (1998) J. Clin. Invest. 101, 327-336.
[20] Bonifacio, E., Genovese, S., Braghi, S., Bazzigaluppi, E., Lampasona, V., Bingley, P. J., Rogge, L., Pastore, M. R., Bognetti, E. and Bottazzo, G. F. (1995) Diabetologia.38, 816-822.
[21] Hermel, J. M., Dirkx, R. and Solimena, M. (1999) Eur. J. Neurosci. 11, 2609-2620.
[22] Solimena, M., Dirkx, R., Hermel, J. M., Pleasic Williams, S., Shapiro, J. A., Caron, L. and Rabin, D. U. (1996) EMBO J. 15, 2102-2114.
[23] Dirkx, R., Hermel, J. M., Rabin, D. U. and Solimena, M. (1998) Adv. Pharmacol. 42, 243-246.
[24] Park, Y. S., Kawasaki, E., Kelemen, K., Yu, L., Schiller, M. R., Rewers, M., Mizuta, M., Eisenbarth, G. S., and Hutton, J. C. (2000) Diabetologia 43, 1293-1301.
[25] Magistrelli, G., Toma, S. e Isacchi, A. (1996) Biochem. Biophys. Res. Commun. 227, 581-588.
[26] Saeki, K., Zhu, M., Kubosaki, A., Xie, J., Lan, M. S. and Notkins, A. L. (2002) Diabetes 51, 1842-1850.
[27] Lampasona, V., Bearzatto, M., Genovese, S., Bosi, E., Ferrari, M. and Bonifacio, E. (1996) J. Immunol. 157, 2707-2711.
[28] Hawkes, C. J., Wasmeier, C., Christie, M. R. and Hutton, J. C. (1996) Diabetes 45,1187-1192.
[29] Bonifacio, E., Lampasona, V., Genovese, S., Ferrari, M. and Bosi, E. (1995) J. Immunol. 155, 5419-5426.
[30] Verge, C. F., Stenger, D., Bonifacio, E., Colman, P. G., Pilcher, C., Bingley, P. J. and Eisenbarth, G. S. (1998) Diabetes 47,1857-1866.
[31] Xie, H., Zhang, B., Matsumoto, Y., Li, Q., Notkins, A. L. and Lan, M. S. (1997) J. Immunol. 159, 3662-3667.
[32] Hatfield, E. C., Hawkes, C. J., Payton, M. A. and Christie, M. R. (1997) Diabetologia 40, 1327-1333.
[33] Morgenthaler, N. G., Lobner, K., Morgenthaler, U. Y., Christie, M. R., Seissler, J. and Scherbaum, W. A. (1998) Horm. Metab. Res. 30, 559-564.
[34] Bonekamp, F., Andersen, H. D., Christensen, T. and Jensen, K. F. (1985) Nucleic Acids Res. 13, 4113-4123.
[35] Kane, J. F. (1995) Curr. Opin. Biotechnol. 6, 494-500.
[36] Morgenthaler, N. G., Lobner, K., Morgenthaler, U. Y., Christie, M. R., Seissler, J., and Scherbaum, W. A. (1998). Horm. Metab. Res. 30, 559-564.
[37] Figueroa, A., Corradini, C., Feibush, B. and Karger, B. L. (1986) J. Chromatogr. 371, 335-352.
[38] MacDonald, R. J., Swift, G. H., Pryzbyla, A. E., and Ghirgwin, J. M. (1987) in *Guide to Molecular Cloning Techniques* (Berger, S. L., and Kimmel, A. R., Eds.) pp 219-227, Academic Press Inc., San Diego.
[39] Gerard, G. F., Fox, D. K., Nathan, M., and D Alessio, J. M. (1997). Molecular Biotechnology 8, 61-77.
[40] Lan, M. S., Lu, J., Goto, Y., and Notkins, A. L. (1994). DNA and Cell Biology 13, 505-14.
[41] Schagger, H., and von Jagow, G. (1987). Anal. Biochem. 166, 368-79.

[42] Berzofsky, J. A., Berkower, I. J. and Epstein, S. L. (1993) en *Fundamental Immunology* (W. E. Paul), pp 421-465, Raven, New York.
[43] Sodoyez Goffaux, F., Koch, M., Dozio, N., Brandenburg, D. and Sodoyez, J. C. (1988) Diabetologia 31, 694-702.
[44] Grubin, C. E., Daniels, T., Toivola, B., Landin-Olsson, M., Hagopian, W. A., Li, L., Karlsen, A. E., Boel, E., Michelsen, B. and Lernmark, A. (1994) Diabetologia 37, 344-350.
[45] Papouchado, M. L., Valdez, S. N., Ghiringhelli, D., Poskus, E. and Ermácora, M. R. (1997) Eur. J. Biochem. 246, 350-359.
[46] Press, W. H., Teukolsky, S. A., Vefterling, W. T., and Flannery, B. P. (1992) *The Art of Scientific Computing*, Cambridge, Univ. Press, New York.
[47] Hof, P., Pluskey, S., Dhe Paganon, S., Eck, M. J. and Shoelson, S. E. (1998) Cell 92, 441-450.
[48] Jia, Z., Barford, D., Flint, A. J. and Tonks, N. K. (1995) Science 268, 1754-1758.
[49] Yang, J., Liang, X., Niu, T., Meng, W., Zhao, Z. and Zhou, G. W. (1998) J. Biol. Chem. 273, 28199-28207.
[50] Lee, M. S., Dirkx, R., Solimena, M. and Dannies, P. S. (1998) Endocrinology 139, 2727-2733.
[51] Christie, M. R., Vohra, G., Champagne, P., Daneman, D. and Delovitch, T. L. (1990) J. Exp. Med. 172, 789-794.
[52] Lobner, K., Khoo Morgenthaler, U. Y., Seissler, J., Morgenthaler, N. G. and Scherbaum, W. A. (1999) Horm. Metab. Res. 31, 686-691.
[53] Pelham, H. R. and Jackson, R. J. (1976) Eur. J. Biochem. 67, 247-256.
[54] Anderson, C., Straus, J. W. and Dudock, B. S. (1985) *in Recombitant Dna Part C* (R. Wu), pp 635-644, Academic Press Inc., San Diego.
[55] Caruthers, M. (1983) in *Methodology of DNA and RNA Sequencing*, Praeger Publishers, New York.

The invention claimed is:

1. A DNA molecule comprising a nucleotide sequence that encodes IA-2ic antigen; wherein said sequence is selected from the group consisting of SEQ ID NO: 1, SEQ ID NO: 2, and SEQ ID NO: 3.

2. The DNA molecule as in claim 1, wherein said sequence consists of SEQ ID NO: 1.

3. The DNA molecule as in claim 1, wherein said sequence consists of SEQ ID NO:2.

4. The DNA molecule as in claim 1, wherein said sequence consists of SEQ ID NO:3.

5. A chimeric DNA molecule comprising a DNA molecule of claim 1, fused with a His-tag encoding sequence.

6. An expression vector comprising the DNA molecule of claim 1.

7. The expression vector of claim 6, wherein the DNA molecule is operatively bound to one or more regulatory sequences that direct expression of the IA-2ic antigen in a bacterial cell.

8. The expression vector of claim 7, wherein the expression vector is a plasmid vector.

9. A transformed host cell, comprising a DNA molecule of claim 1.

10. The cell of claim 9, wherein said cell is a prokaryotic cell.

11. The cell of claim 10, wherein said cell is an *Escherichia coli* cell.

12. A method of producing a polypeptide of human IA-2ic antigen, which comprises growing cells transformed with a DNA molecule of claim 1, under conditions suitable for the production of said polypeptide.

13. The method of claim 12, wherein the transformed cells are *Escherichia coli* cells.

14. A method of producing a polypeptide of human IA-sic antigen, which comprises the stage of:
  a) transforming the *Escherichia coli* cells with the plasmid of claim 8;
  b) growing the transformed cells at 37° C.,
  c) inducing protein expression with IPTG;
  d) collecting the cells;
  e) lysing the collected cells; and
  f) isolating the polypeptide.

* * * * *

SEQUENCE LISTING

<160> NUMBER OF SEQ ID NOS: 15

<210> SEQ ID NO 1
<211> LENGTH: 1746
<212> TYPE: DNA
<213> ORGANISM: Artificial Sequence
<220> FEATURE:
<223> OTHER INFORMATION: Nucleotide sequence that encodes the
      intracellular domain IA-2ic. Base position 1=1868; Base position
      2=1869; etc.

<400> SEQUENCE: 1

```
catatgcggc agcatgcgcg gcagcaagac aaggagcgcc tggcagccct ggggcctgag      60
ggggcccatg gtgacactac ctttgagtac caggacctgt gccgccagca catggccacg     120
aagtccttgt tcaaccgggc agagggtcca ccggagcctt cacgggtgag cagtgtgtcc     180
tcccagttca gcgacgcagc ccaggccagc cccagctccc acagcagcac cccgtcctgg     240
tgcgaggagc cggcccaagc caacatggac atctccacgg gacacatgat tctggcatac     300
atggaggatc acctgcggaa ccgggaccgc cttgccaagg agtggcaggc cctctgtgcc     360
taccaagcag agccaaacac ctgtgccacc gcgcagggg agggcaacat caaaaagaac     420
cggcatcctg acttcctgcc ctatgaccat gcccgcataa aactgaaggt ggagagcagc     480
ccttctcgga gcgattacat caacgccagc cccattattg agcatgaccc tcggatgcca     540
gcctacatag ccacgcaggg cccgctgtcc cataccatcg cagacttctg gcagatggtg     600
tgggagagcg gctgcaccgt catcgtcatg ctgacccgc tggtggagga tggtgtcaag     660
cagtgtgacc gctactggcc agatgagggt gcctccctct accacgtata tgaggtgaac     720
ctggtgtcgg agcacatctg gtgcgaggac tttctggtgc ggagcttcta cctgaagaac     780
gtgcagaccc aggagacgcg cacgctcacg cagttccact tcctcagctg gccggcagag     840
ggcacaccgg cctccacgcg gcccctgctg gacttccgcc gtaaggtgaa caagtgctac     900
cggggccgct cctgccccat catcgtgcac tgcagtgatg gtgcggggcg taccggcacc     960
tacatcctca tcgacatggt cctgaaccgc atggcaaaag gagtgaagga gattgacatc    1020
gctgccaccc tggagcatgt ccgtgaccag cggcctggcc ttgtccgctc taaggaccag    1080
tttgaatttg ccctgacagc cgtggcggag gaagtgaatg ccatcctcaa ggccctgccc    1140
cagtgagacc ctggggcccc ttggcgggca gcccagcctc tgtccctctt tgcctgtgtg    1200
```

```
agcatctctg tgtacccact cctcactgcc ccaccagcca cctcttgggc atgctcagcc    1260
cttcctagaa gagtcaggaa gggaaagcca gaaggggcac gcctgcccag cctcgcatgc    1320
cagagcctgg ggcatcccag agcccagggc atcccatggg ggtgctgcag ccaggaggag    1380
aggaaaggac atgggtagca attctaccca gagccttctc ctgcctacat tccctggcct    1440
ggctctcctg tagctctcct ggggttctgg gagttccctg aacatctgtg tgtgtccccc    1500
tatgctccag tatggaagaa tggggtggag ggtcgccaca cccggctccc cctgcttctc    1560
agccccgggc ctgcctctga ctcacacttg ggcgctctgc cctccctggc ctcacgccca    1620
gcctggtccc accaccctcc caccatgcgc tgctcaacct ctctccttct ggcgcaagag    1680
aacatttcta gaaaaaacta cttttgtacc agtgtgaata agttagtgt gttgtctgtg    1740 cagctg                                                              1746

<210> SEQ ID NO 2
<211> LENGTH: 1746
<212> TYPE: DNA
<213> ORGANISM: Artificial Sequence
<220> FEATURE:
<223> OTHER INFORMATION: Nucleotide sequence that encodes for
      intracellular domain of IA-2ic.  Base position 1=1868; 2=1869;
      etc.

<400> SEQUENCE: 2
catatgcggc agcatgcgcg gcagcaagac aaggagcgcc tggcagccct ggggcctgag     60
ggggcccatg gtgacactac ctttgagtac caggacctgt gccgccagca catggccacg    120
aagtccttgt tcaaccgggc agagggtcca ccggagcctt cacgggtgag cagtgtgtcc    180
tcccagttca gcgacgcagc ccaggccagc cccagctccc acagcagcac cccgtcctgg    240
tgcgaggagc cggcccaagc caacatggac atctccacgg acacatgat tctggcatac    300 atggaggatc acctgcggaa ccgggaccgc cttgccaagg agtggcaggc cctctgtgcc    360
taccaagcag agccaaacac ctgtgccacc gcgcaggggg agggcaacat caaaaagaac    420
cggcatcctg acttcctgcc ctatgaccat gcccgcataa aactgaaggt ggagagcagc    480
ccttctcgga gcgattacat caacgccagc cccattattg agcatgaccc tcggatgcca    540
gcctacatag ccacgcaggg cccgctgtcc ataccatcg cagacttctg gcagatggtg    600
tgggagagcg gctgcaccgt catcgtcatg ctgaccccgc tggtggagga tggtgtcaag    660
cagtgtgacc gctactggcc agatgagggt gcctccctct accacgtata tgaggtgaac    720
ctggtgtcgg agcacatctg tgtcgaggac tttctggtgc ggagcttcta cctgaagaac    780
gtgcagaccc aggagacgcg cacgctcacg cagttccact cctcagctg gccggcagag    840 ggcacaccgg cctccacgcg gcccctgctg gacttccgcc gtaaggtgaa caagtgctac    900 cgggccgct cctgccccat catcgtgcac tgcagtgatg gtgcggggag gaccggcacc    960
tacatcctca tcgacatggt cctgaaccgc atggcaaaag gagtgaagga gattgacatc   1020
gctgccaccc tggagcatgt ccgtgaccag cggcctggcc ttgtccgctc taaggaccag   1080
tttgaatttg ccctgacagc cgtggcgag gaagtgaatg ccatcctcaa ggccctgccc   1140
cagtgagacc ctggggcccc ttggcggca gcccagcctc tgtccctctt tgcctgtgtg   1200
agcatctctg tgtacccact cctcactgcc ccaccagcca cctcttgggc atgctcagcc   1260
cttcctagaa gagtcaggaa gggaaagcca gaaggggcac gcctgcccag cctcgcatgc   1320
cagagcctgg ggcatcccag agcccagggc atcccatggg ggtgctgcag ccaggaggag   1380
```

| | |
|---|---|
| aggaaaggac atgggtagca attctaccca gagccttctc ctgcctacat tccctggcct | 1440 |
| ggctctcctg tagctctcct ggggttctgg gagttccctg aacatctgtg tgtgtccccc | 1500 |
| tatgctccag tatggaagaa tggggtggag ggtcgccaca cccggctccc cctgcttctc | 1560 |
| agccccgggc ctgcctctga ctcacacttg ggcgctctgc cctccctggc ctcacgccca | 1620 |
| gcctggtccc accaccctcc caccatgcgc tgctcaacct ctctccttct ggcgcaagag | 1680 |
| aacatttcta gaaaaaacta cttttgtacc agtgtgaata agttagtgt gttgtctgtg | 1740 |
| cagctg | 1746 |

<210> SEQ ID NO 3
<211> LENGTH: 1746
<212> TYPE: DNA
<213> ORGANISM: Artificial Sequence
<220> FEATURE:
<223> OTHER INFORMATION: Nucleotide sequence that encodes for the
      intracellular domain of IA-2ic. Base position 1=1868; base
      position 2=1869; etc.

<400> SEQUENCE: 3

| | |
|---|---|
| catatgcggc agcatgcgcg gcagcaagac aaggagcgcc tggcagccct ggggcctgag | 60 |
| ggggcccatg gtgacactac ctttgagtac caggacctgt gccgccagca catggccacg | 120 |
| aagtccttgt tcaaccgggc agagggtcca ccggagcctt cacgggtgag cagtgtgtcc | 180 |
| tcccagttca gcgacgcagc ccaggccagc cccagctccc acagcagcac cccgtcctgg | 240 |
| tgcgaggagc cggcccaagc caacatggac atctccacgg gacacatgat tctggcatac | 300 |
| atggaggatc acctgcggaa ccgggaccgc cttgccaagg agtggcaggc cctctgtgcc | 360 |
| taccaagcag agccaaacac ctgtgccacc gcgcaggggg agggcaacat caaaaagaac | 420 |
| cggcatcctg acttcctgcc ctatgaccat gcccgcataa aactgaaggt ggagagcagc | 480 |
| ccttctcgga gcgattacat caacgccagc cccattattg agcatgaccc tcggatgcca | 540 |
| gcctacatag ccacgcaggg cccgctgtcc cataccatcg cagacttctg gcagatggtg | 600 |
| tgggagagcg gctgcaccgt catcgtcatg ctgaccccgc tggtggagga tggtgtcaag | 660 |
| cagtgtgacc gctactggcc agatgagggt gcctccctct accacgtata tgaggtgaac | 720 |
| ctggtgtcgg agcacatctg gtgcgaggac tttctggtgc ggagcttcta cctgaagaac | 780 |
| gtgcagaccc aggagacgcg cacgctcacg cagttccact tcctcagctg gccggcagag | 840 |
| ggcacaccgg cctccacgcg gccccctgctg gacttccgca ggaaggtgaa caagtgctac | 900 |
| cggggccgct cctgccccat catcgtgcac tgcagtgatg gtgcggggcg taccggcacc | 960 |
| tacatcctca tcgacatggt cctgaaccgc atggcaaaag gagtgaagga gattgacatc | 1020 |
| gctgccaccc tggagcatgt ccgtgaccag cggcctggcc ttgtccgctc taaggaccag | 1080 |
| tttgaatttg ccctgacagc cgtggcggag gaagtgaatg ccatcctcaa ggccctgccc | 1140 |
| cagtgagacc ctggggcccc ttggcgggca gcccagcctc tgtccctctt tgcctgtgtg | 1200 |
| agcatctctg tgtacccact cctcactgcc ccaccagcca cctcttgggc atgctcagcc | 1260 |
| cttcctagaa gagtcaggaa gggaaagcca gaaggggcac gcctgcccag cctcgcatgc | 1320 |
| cagagcctgg ggcatcccag agccagggc atcccatggg ggtgctgcag ccaggaggag | 1380 |
| aggaaaggac atgggtagca attctaccca gagccttctc ctgcctacat tccctggcct | 1440 |
| ggctctcctg tagctctcct ggggttctgg gagttccctg aacatctgtg tgtgtccccc | 1500 |
| tatgctccag tatggaagaa tggggtggag ggtcgccaca cccggctccc cctgcttctc | 1560 |
| agccccgggc ctgcctctga ctcacacttg ggcgctctgc cctccctggc ctcacgccca | 1620 |

```
gcctggtccc accaccctcc caccatgcgc tgctcaacct ctctccttct ggcgcaagag    1680
aacatttcta gaaaaaacta cttttgtacc agtgtgaata agttagtgt gttgtctgtg     1740 cagctg                                                                1746
```

<210> SEQ ID NO 4
<211> LENGTH: 3613
<212> TYPE: DNA
<213> ORGANISM: Artificial Sequence
<220> FEATURE:
<223> OTHER INFORMATION: Nucleotide sequence of the complete IA-2 gene.

<400> SEQUENCE: 4

```
cagcccctct ggcaggctcc cgccagcgtc gctgcggctc cggcccggga gcgagcgccc      60
ggagctcgga aagatgcggc gcccgcggcg gcctgggggt ctcggggat ccggggtct      120 ccggctgctc ctctgcctcc tgctgctgag cagccgcccg gggggctgca cgccgttag      180 tgcccacggc tgtctatttg accgcaggct ctgctctcac ctggaagtct gtattcagga     240
tggcttgttt gggcagtgcc aggtgggagt ggggcaggcc cggcccccttt tgcaagtcac     300 ctccccagtt ctccaacgct acaaggtgt gctccgacaa ctcatgtccc aaggattgtc      360
ctggcacgat gacctcaccc agtatgtgat ctctcaggag atggagcgca tcccaggct      420 tcgcccccca gagcccgtc caagggacag gtctggcttg caccccaaga gacctggtcc      480
tgctggagag ctgcttttac aggacatccc cactggctcc gccccctgctg ccagcatcg      540 gcttccacaa ccaccagtgg gcaaaggtgg agctggggcc agctcctctc tgtccctct      600 gcaggctgag ctgctcccgc ctctcttgga gcacctgctg ctgccccac agcctcccca      660 cccttcactg agttacgaac ctgccttgct gcagccctac ctgttccacc agtttggctc      720
ccgtgatggc tccagggtct cagagggctc ccagggatg gtcagtgtcg gccccctgcc      780
caaggctgaa gcccctgccc tcttcagcag aactgcctcc aagggcatat ttggggacca      840
ccctggccac tcctacgggg accttccagg gccttcacct gcccagctttt tcaagactc     900 tgggctgctc tatctggccc aggagttgcc agcacccagc agggccaggg tgccaaggct      960
gccagagcaa gggagcagca gccgggcaga ggactcccca gagggctatg agaaggaagg     1020 actagggat cgtggagaga agcctgcttc cccagctgtg cagccagatg cggctctgca     1080
gaggctggcc gctgtgctgg cgggctatgg ggtagagctg cgtcagctga cccctgagca     1140
gctctccaca ctcctgaccc tgctgcagct actgccaag ggtgcaggaa gaaatccggg      1200 agggttgta atgttggag ctgatatcaa gaaaacaatg gagggccgg tggagggcag       1260 agacacagca gagcttccag ccgcacatc ccccatgcct ggacacccca ctgccagccc     1320
tacctccagt gaagtccagc aggtgccaag ccctgtctcc tctgagcctc ccaaagctgc     1380 cagacccct gtgacacctg tcctgctaga aagaaaagc ccactgggcc agagccagcc     1440
cacggtggca ggacagccct cagcccgccc agcagcagag gaatatggct acatcgtcac     1500
tgatcagaag cccctgagcc tggctgcagg agtgaagctg ctggagatcc tggctgagca     1560
tgtgcacatg tcctcaggca gcttcatcaa catcagtgtg gtgggaccag ccctcacctt     1620
ccgcatccgg cacaatgagc agaacctgtc tttggctgat gtgacccaac aagcagggct     1680
ggtgaagtct gaactggaag cacagacagg gctccaaatc ttgcagacag gagtgggaca     1740
gagggaggag gcagctgcag tccttcccca aactgcgcac agcacctcac ccatgcgctc     1800
agtgctgctc actctggtgg ccctggcagg tgtggctggg ctgctggtgg ctctggctgt     1860
```

-continued

```
ggctctgtgt gtgcggcagc atgcgcggca gcaagacaag gagcgcctgg cagccctggg    1920
gcctgagggg gcccatggtg acactacctt tgagtaccag gacctgtgcc gccagcacat    1980
ggccacgaag tccttgttca accgggcaga gggtccaccg gagccttcac gggtgagcag    2040
tgtgtcctcc cagttcagcg acgcagccca ggccagcccc agctcccaca gcagcacccc    2100
gtcctggtgc gaggagccgg cccaagccaa catggacatc tccacgggac acatgattct    2160
ggcatacatg gaggatcacc tgcggaaccg ggaccgcctt gccaaggagt ggcaggccct    2220
ctgtgcctac caagcagagc caaacacctg tgccaccgcg caggggggagg gcaacatcaa    2280
aaagaaccgg catcctgact tcctgcccta tgaccatgcc cgcataaaac tgaaggtgga    2340
gagcagccct tctcggagcg attacatcaa cgccagcccc attattgagc atgaccctcg    2400
gatgccagcc tacatagcca cgcagggccc gctgtcccat accatcgcag acttctggca    2460
gatggtgtgg gagagcggct gcaccgtcat cgtcatgctg accccgctgg tggaggatgg    2520
tgtcaagcag tgtgaccgct actggccaga tgagggtgcc tccctctacc acgtatatga    2580
ggtgaacctg gtgtcggagc acatctggtg cgaggacttt ctggtgcgga gcttctacct    2640
gaagaacgtg cagacccagg agacgcgcac gctcacgcag ttccacttcc tcagctggcc    2700
ggcagagggc acaccggcct ccacgcggcc cctgctggac ttccgcagga aggtgaacaa    2760
gtgctaccgg ggccgctcct gccccatcat cgtgcactgc agtgatggtg cggggaggac    2820
cggcacctac atcctcatcg acatggtcct gaaccgcatg gcaaaaggag tgaaggagat    2880
tgacatcgct gccaccctgg agcatgtccg tgaccagcgg cctggccttg tccgctctaa    2940
ggaccagttt gaatttgccc tgacagccgt ggcggaggaa gtgaatgcca tcctcaaggc    3000
cctgccccag tgagaccctg gggcccttg gcgggcagcc cagcctctgt ccctctttgc    3060
ctgtgtgagc atctctgtgt acccactcct cactgcccca ccagccacct cttgggcatg    3120
ctcagccctt cctagaagag tcaggaaggg aaagccagaa ggggcacgcc tgcccagcct    3180
cgcatgccag agcctggggc atcccagagc ccagggcatc ccatgggggt gctgcagcca    3240
ggaggagagg aaaggacatg ggtagcaatt ctacccagag ccttctcctg cctacattcc    3300
ctggcctggc tctcctgtag ctctcctggg gttctgggag ttccctgaac atctgtgtgt    3360
gtcccctat gctccagtat ggaagaatgg ggtggagggt cgccacaccc ggctcccct    3420
gcttctcagc cccgggcctg cctctgactc acacttgggc gctctgccct ccctggcctc    3480
acgcccagcc tggtcccacc accctcccac catgcgctgc tcaacctctc tccttctggc    3540
gcaagagaac atttctagaa aaaactactt ttgtaccagt gtgaataaag ttagtgtgtt    3600
gtctgtgcag ctg                                                        3613
```

<210> SEQ ID NO 5
<211> LENGTH: 26
<212> TYPE: DNA
<213> ORGANISM: Artificial Sequence
<220> FEATURE:
<223> OTHER INFORMATION: Initiator polynucleotide (2797c) used during
      the cloning and mutagenesis processes.

<400> SEQUENCE: 5
ctgcagtgat ggtgccggcc gtaccg                                           26

<210> SEQ ID NO 6
<211> LENGTH: 26
<212> TYPE: DNA
<213> ORGANISM: Artificial Sequence
<220> FEATURE:

```
<223> OTHER INFORMATION: Initiator polynucleotide (2797cDG) used during
      the cloning and mutagenesis processes.

<400> SEQUENCE: 6
ctgcagtggt ggtgccggcc gtaccg                                            26

<210> SEQ ID NO 7
<211> LENGTH: 27
<212> TYPE: DNA
<213> ORGANISM: Artificial Sequence
<220> FEATURE:
<223> OTHER INFORMATION: Initiator polynucleotide (2741cF) used during
      the cloning and mutagenesis processes.

<400> SEQUENCE: 7
ttccgccgta aggtgaacaa gtgctac                                           27

<210> SEQ ID NO 8
<211> LENGTH: 28
<212> TYPE: DNA
<213> ORGANISM: Artificial Sequence
<220> FEATURE:
<223> OTHER INFORMATION: Initiator polynucleotide (2741cR) used during
      the cloning and mutagenesis processes.

<400> SEQUENCE: 8
tgttcacctt acggcggaag tccagcag                                          28

<210> SEQ ID NO 9
<211> LENGTH: 45
<212> TYPE: DNA
<213> ORGANISM: Artificial Sequence
<220> FEATURE:
<223> OTHER INFORMATION: Initiator polynucleotide (A877D) used during
      the cloning and mutagenesis processes.

<400> SEQUENCE: 9
ctcacgcagt tccacttcct cagctggccg gatgagggta caccg                       45

<210> SEQ ID NO 10
<211> LENGTH: 26
<212> TYPE: DNA
<213> ORGANISM: Artificial Sequence
<220> FEATURE:
<223> OTHER INFORMATION: Initiator polynucleotide (IcNde) used during
      the cloning and mutagenesis processes.

<400> SEQUENCE: 10
catatgcggc aacaagacaa ggagcg                                            26

<210> SEQ ID NO 11
<211> LENGTH: 26
<212> TYPE: DNA
<213> ORGANISM: Artificial Sequence
<220> FEATURE:
<223> OTHER INFORMATION: Initiator polynucleotide (IcaR) used during the
      cloning and mutagenesis processes.

<400> SEQUENCE: 11
cagtgaggag tgggtacaca gagatg                                            26

<210> SEQ ID NO 12
<211> LENGTH: 21
<212> TYPE: DNA
<213> ORGANISM: Artificial Sequence
<220> FEATURE:
<223> OTHER INFORMATION: Initiator polynucleotide (IcaF) used during the
```

-continued

```
        cloning and mutagenesis processes.

<400> SEQUENCE: 12
gcggcagcaa gacaagaagc g                                              21

<210> SEQ ID NO 13
<211> LENGTH: 63
<212> TYPE: DNA
<213> ORGANISM: Artificial Sequence
<220> FEATURE:
<223> OTHER INFORMATION: Initiator polynucleotide (3'THisBam) used
      during the cloning and mutagenesis processes.

<400> SEQUENCE: 13
ggatcctcag tgatggtgat ggtgatggct gccgcgcggc accagctggg gaagggcctt    60
gag                                                                  63

<210> SEQ ID NO 14
<211> LENGTH: 26
<212> TYPE: DNA
<213> ORGANISM: Artificial Sequence
<220> FEATURE:
<223> OTHER INFORMATION: Initiator polynucleotide (3095BamHI) used
      during the cloning and mutagenesis processes.

<400> SEQUENCE: 14
cagtgaggag tgggatccca gagatg                                         26

<210> SEQ ID NO 15
<211> LENGTH: 37
<212> TYPE: DNA
<213> ORGANISM: Artificial Sequence
<220> FEATURE:
<223> OTHER INFORMATION: Initiator polynucleotide (KozIC) used during
      the cloning and mutagenesis processes.

<400> SEQUENCE: 15
tctagaccac catggcgcga cagcaagaca aagagcg                             37
```